United States Patent
Kontur et al.

(10) Patent No.: US 11,426,271 B2
(45) Date of Patent: Aug. 30, 2022

(54) TRIFOCAL ARTIFICIAL OPHTHALMIC LENS AND METHOD FOR ITS PRODUCTION

(71) Applicant: MEDICONTUR ORVOSTECHNIKAI KFT., Zsambek (HU)

(72) Inventors: Laszlo Ferenc Kontur, Budapest (HU); Daniel Bercsenyi, Erd (HU); Gabor Erdei, Budapest (HU); Bence Papdi, Szeged (HU)

(73) Assignee: MEDICONTUR ORVOSTECHNIKAI KFT.

( * ) Notice: Subject to any disclaimer, the term of this patent is extended or adjusted under 35 U.S.C. 154(b) by 151 days.

(21) Appl. No.: 16/956,834

(22) PCT Filed: Dec. 28, 2018

(86) PCT No.: PCT/HU2018/050054
§ 371 (c)(1),
(2) Date: Jun. 22, 2020

(87) PCT Pub. No.: WO2019/130031
PCT Pub. Date: Jul. 4, 2019

(65) Prior Publication Data
US 2021/0361414 A1 Nov. 25, 2021

(30) Foreign Application Priority Data
Dec. 28, 2017 (HU) .................................. P1700548

(51) Int. Cl.
*A61F 2/16* (2006.01)
*G02C 7/06* (2006.01)

(52) U.S. Cl.
CPC .......... *A61F 2/1618* (2013.01); *A61F 2/1654* (2013.01); *G02C 7/06* (2013.01)

(58) Field of Classification Search
CPC ............................ A61F 2/1618; A61F 2/1654
See application file for complete search history.

(56) References Cited

U.S. PATENT DOCUMENTS

| 5,121,980 A | 6/1992 | Cohen |
| 7,871,162 B2 | 1/2011 | Weeber |

(Continued)

*Primary Examiner* — Javier G Blanco
(74) *Attorney, Agent, or Firm* — Olson & Cepuritis, Ltd.

(57) ABSTRACT

The invention relates to a trifocal artificial ophthalmic lens (20), which contains an anterior side optical surface (21), a posterior side optical surface (22) and an optical axis (23), at least one of the anterior side optical surface (21) and the posterior side optical surface (22) contains an optics having three useful focal points and having an at least partially diffractive profile. The three useful focal points correspond to focal points (31, 32) belonging to the $0^{th}$ and $1^{st}$ diffraction orders of the diffractive profile, and to a focal point (33) belonging to an enhanced diffractive secondary peaks between the $0^{th}$ and the $1^{st}$ diffraction orders. The invention also relates to a method of producing the aforementioned trifocal artificial ophthalmic lens.

6 Claims, 5 Drawing Sheets

(56) References Cited

U.S. PATENT DOCUMENTS

| | | | |
|---|---|---|---|
| 2007/0182924 A1* | 8/2007 | Hong | A61F 2/1654 351/159.43 |
| 2009/0122262 A1 | 5/2009 | Hong et al. | |
| 2010/0100178 A1 | 4/2010 | Weeber et al. | |
| 2011/0292335 A1* | 12/2011 | Schwiegerling | A61F 2/1656 623/6.11 |
| 2012/0140166 A1* | 6/2012 | Zhao | G02C 7/041 351/159.44 |
| 2014/0347624 A1* | 11/2014 | Ando | A61F 2/1654 351/159.73 |
| 2017/0245986 A1* | 8/2017 | Canovas Vidal | G02B 27/0075 |

* cited by examiner

TRIFOCAL ARTIFICIAL OPHTHALMIC LENS AND METHOD FOR ITS PRODUCTION

CROSS-REFERENCE TO RELATED APPLICATIONS

This application is a U.S. National Stage of PCT/HU2018/050054, filed Dec. 28, 2018, which claims priority to Hungarian Patent Application No. P1700548, filed Dec. 28, 2017, each of which is incorporated herein by reference.

THE OBJECT OF THE INVENTION

The object of the invention relates to a trifocal artificial ophthalmic lens, which artificial ophthalmic lens may be an artificial lens that may be implanted in the capsular bag, the ciliary sulcus or in the anterior chamber, it may be a contact lens, or an artificial lens that can be implanted in the cornea using an inlay or onlay technique. The object of the invention also relates to a method for the production of the aforementioned trifocal artificial ophthalmic lens.

THE STATE OF THE ART

The human crystalline lens transmits the large proportion of the visible range of the electromagnetic spectrum, however, as a result of advanced age, trauma or extreme doses of UV or x-ray radiation the human eye may gradually become cloudy, which condition is called cataract. In addition congenital cataract also exists, which can be inherited or the result of an infection during pregnancy. At present the only effective way of treating cataract is the removal of the clouded lens and the replacement of the refractive power of the lens with an implanted artificial ophthalmic lens.

A further indication for the implanting of an artificial ophthalmic lens may be a refractive defect of such an extent the correction of which is not or only partially possible with spectacles, contact lenses or corneal laser surgery. This procedure is simply called refractive lens exchange.

Up until the second half of the nineteen-eighties implanted artificial ophthalmic lenses were only monofocal lenses that formed a sharp image on the retina of objects at a given distance (usually further than 4 metres away).

The refractive multifocal artificial ophthalmic lenses available from the nineteen-nineties contain concentric or asymmetric zones with differing refractive power. Their disadvantage is that their optical performance strongly depends on pupil size, in addition the intensity distribution of the incoming light in the vicinity of the retina does not vary smoothly as a function of the pupil diameter.

The diffractive bifocal artificial ophthalmic lenses appearing in the 2000-s were also capable of creating sharp images on the retina of objects at reading distance (approximately 35 to 40 cm), however these artificial ophthalmic lenses were also unable to replace the accommodating ability of the natural human eye lens.

As a result of the increasingly widespread activities today performed with screens, the significance of the quality of images at intermediate distances (approximately 60 to 80 cm) has increased. The diffractive trifocal artificial ophthalmic lenses widely used by the 2010-s are able to satisfy this demand.

With the progression of age the accommodating ability of the eye deteriorates as a result of the drop in flexibility of the natural human crystalline lens and of the weakening of the ciliary muscles. This eye-ageing condition is called presbyopia. Due to the availability of trifocal and extended depth of focus (EDOF) artificial ophthalmic lenses, artificial ophthalmic lens implants for other than cataract surgery do not only represent a purely refractive lens exchange, their purpose may also be to make up for accommodation ability. As implants made for reasons other than cataract surgery characteristically involve the younger (45- to 50-year-old) active age group, there is a significant demand for sharp sight at working distances (60 to 80 cm) in addition to far and near distances.

Patent specification number U.S. Pat. No. 5,121,980 (Cohen) describes that the secondary peak falling between the $0^{th}$ diffraction order and the $1^{st}$ diffraction order may be minimized with the shifting of the phase displacement zones in a direction perpendicular to the optical axis in such a way that the maximum phase shift of the central phase shifting zone is $\lambda/4$, where $\lambda$ is the wavelength of the light for which the diffractive optical element is designed.

Patent specification number EP2045648B1 (Simpson et al.) discloses a refractive-diffractive multifocal lens that has a refractive central zone. The central zone has a focal distance required for far sight (or near or intermediate). The limitation of the solution is that the central zone can only be treated as a refractive optical element if the pupil diameter is equal to or less than the diameter of the central zone.

Patent application number US 2010/0131060 A1 (Simpson et al.) describes a refractive-diffractive multifocal lens that has a refractive central zone and the intensity at the focal point of the central zone (far, near or intermediate) is increased, and the image creation quality (modulation transfer function, MTF) of the multifocal lens containing such a refractive central zone is optimized for the far focus. The limitation of the solution is that the central zone may only be treated as a refractive optical element if the pupil diameter is equal to or less than the diameter of the central zone.

Patent specification number U.S. Pat. No. 5,344,447 A (Swanson) describes a diffractive binary (Dammann) surface profile that creates three foci by amplifying the $-1^{st}$, the $0^{th}$ and the $+1^{st}$ diffraction orders. The disadvantage of this solution is that the intensity ratios falling on the $-1^{st}$ and $+1^{st}$ orders are the same and cannot be changed independently of each other.

Patent specification number EP2503962 (A1) (Houbrechts et al.) presents a design method the basis of which is the combination of two bifocal diffractive surface profiles, where the first diffraction order of the so-called first diffractive surface profile and the second diffraction order of the so-called second diffractive surface profile coincide. Consequentially, the three focus points are created by the $0^{th}$, $+1^{st}$ and the $+2^{nd}$ diffraction orders within the superimposed diffractive surface profile.

Patent application number US2011292335 (A1) (Schwiegerling) discloses a diffractive surface profile in which the height of the steps of the even numbered and odd numbered, counted from the optical axis, phase shift elements changes. Another possible embodiment of the solution is a diffractive surface profile in which the height of the steps of the even numbered and odd numbered, counted from the optical axis, phase shift elements changes and the step heights of the even numbered and odd numbered phase shift elements are individually changed by individual apodization functions. Such diffractive surface profiles also achieve the trifocal optical performance with the amplification of the $0^{th}$, the $+1^{st}$ and $+2^{nd}$ diffraction orders.

Patent application number U520070182921 A1 (Zhand et al.) describes the simultaneous use of a traditional saw tooth type, bifocal optical diffractive surface profile (in the outer zone of the intraocular lens) and of a binary (Dammann) type trifocal optical diffractive surface profile (in the inner zone of the intraocular lens). The disadvantage of this solution is also that in the case of small pupil sizes the intensity ratios in the $-1^{st}$ and $+1^{st}$ diffraction orders are the same and cannot be changed independently of each other.

The common disadvantage of the solutions presented in the latter four patent specifications is that the creation of a second diffractive order involves unavoidable light loss and undesirable light scatter.

A BRIEF SUMMARY OF THE INVENTION

The objective of the invention is to overcome the deficiencies of the known solutions at least partially and to create a multifocal artificial ophthalmic lens that, as artificial ophthalmic lens, ensures intermediate and near vision in addition to far vision (distant vision).

It was recognised that by enhancing the diffractive secondary peaks occurring between the $0^{th}$ and the $1^{st}$ diffraction orders a trifocal lens can be designed that fulfils the aforementioned objective without the creation of further diffractive orders, in other words the $0^{th}$ diffraction order of the artificial ophthalmic lens with the diffractive profile creates sharp images of distant objects (object distance greater than 4 m) on the retina, the $1^{st}$ diffraction order of the artificial ophthalmic lens with the diffractive profile creates sharp images of near objects (object distance: 30 to 40 cm) on the retina, and the enhanced secondary peak of the artificial ophthalmic lens with the diffractive profile creates sharp images of intermediate objects (object distance: 60-80 cm) on the retina.

In other words the object of the invention relates to a trifocal (multifocal) artificial ophthalmic lens that contains an anterior side optical surface, a posterior side optical surface and an optical axis, at least one of the anterior side optical surface and the posterior side optical surface contains an optics having three useful focal points and having at least a partially diffractive profile. It is characteristic of the invention that the three useful focuses are realised by the focal points belonging to the $0^{th}$ and $1^{st}$ diffraction order of the diffractive profile, and by the focal point belonging to the enhanced diffractive secondary peaks falling between the focal points belonging to the $0^{th}$ and the $1^{st}$ diffraction orders.

The object of the invention also relates to a method with which the above artificial ophthalmic lens can be produced.

As the artificial ophthalmic lens described in the present invention may be an artificial lens implanted in the capsular bag, the ciliary sulcus or in the anterior chamber, or may be a contact lens, or an artificial lens that can be implanted in the cornea using an inlay or onlay technique, therefore the disclosed embodiments may be used at any of the aforementioned locations.

A DETAILED DESCRIPTION OF THE EMBODIMENTS ACCORDING TO THE INVENTION

Figure 1:
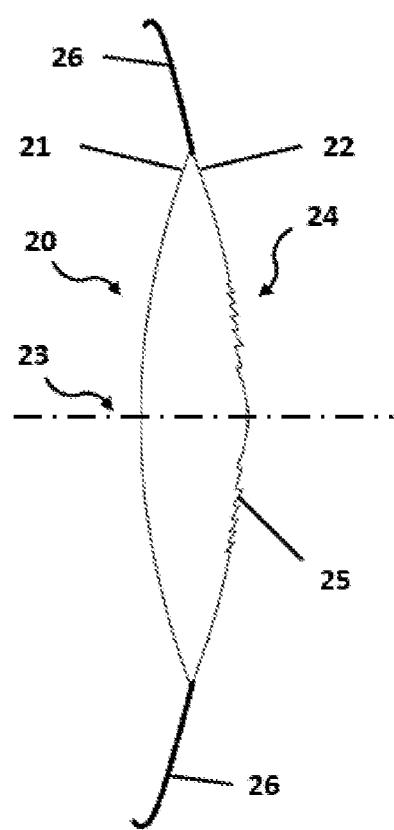
FIG. 1 depicts a schematic side view of an embodiment of the present invention.

FIG. 1 depicts a schematic side view of an embodiment of the present invention, in which it can be seen that the artificial ophthalmic lens 20 contains an anterior optical surface 21 and a posterior optical surface 22. The anterior optical surface 21 and the posterior optical surface 22 have a common optical axis 23, and the posterior optical surface 22 is formed as a multifocal optics 24 with a diffractive profile 25. The present embodiment is also provided with haptics 26, as an implantable artificial lens is depicted.

Figure 2:
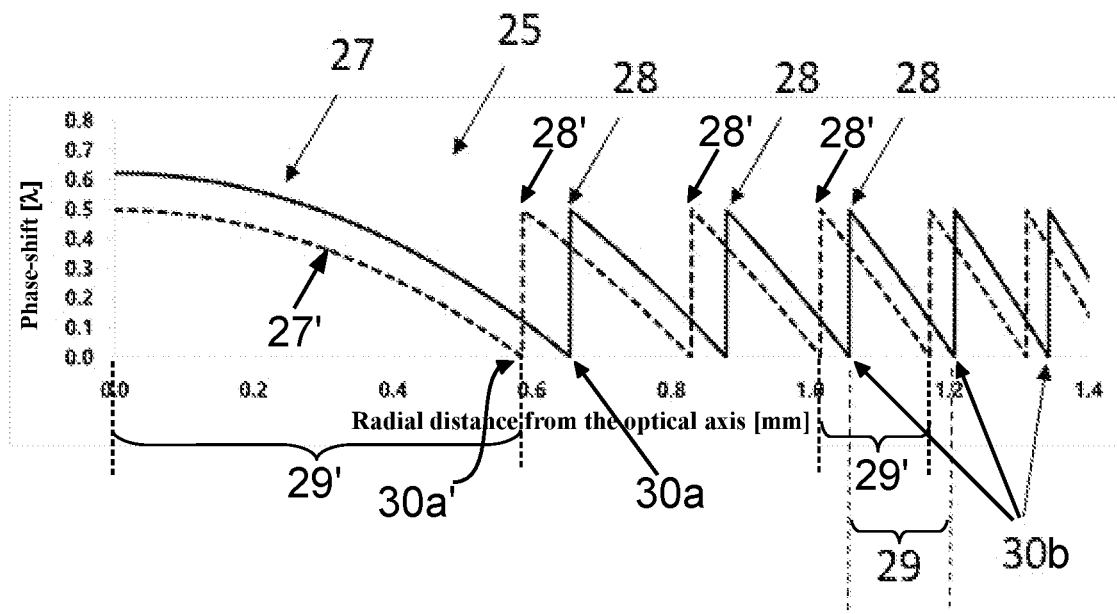
FIG. 2 depicts the phase shift produced by a saw-tooth-type, non-apodized diffractive profile as a function of distance measured from the optical axis, where the maximum phase shift of the central zone is $5/8\lambda$.

In a preferred embodiment the maximum phase shift of the central zone 27 of the diffractive profile 25 is greater than $\lambda/2$ and smaller than $3/4\lambda$, where $\lambda$ is the wavelength of the light for which the operation of the diffractive optical element is designed. FIG. 2 depicts a saw-tooth-type diffractive profile 25 as a function of distance measured from the optical axis 23, where the maximum phase shift of the central zone 27 is $5/8\lambda$, where phase shift means the phase shift relative to the base defined by base points 30a of the diffractive profile. The diffractive profile 25 presented is non-apodized, in other words the heights of the phase shifting zones 28 outside of the central zone 27 are identical. The dashed line in the figure displays the original profile, while the solid line illustrates the modification according to the invention. The original profile displays the diffractive structure of a conventional bifocal lens known by itself, in the case of which the bifocality is ensured by that the maximum phase shift of the individual zones is $\lambda/2$, while the areas 29' between the zone borders of the individual zones are of the same size, in other words the areas 29' of the phase shifting zones 28' outside the central zone 27' of the original profile 27' are the same as the area 29' delimited by the central zone 27', as is known from the literature by a person skilled in the art. The arc linking the base points 30a of the central zone 27 in the diffractive profile according to the invention (of which base points 30a only one is indicated) is parallel to the arc linking the base points 30a' of the central zone 27' of the original profile, and the areas 29 between the zone boundaries of the phase shifting zones 28 are of the same size as the area 29' occupied by the central zone 27' of the original profile.

Figure 3:
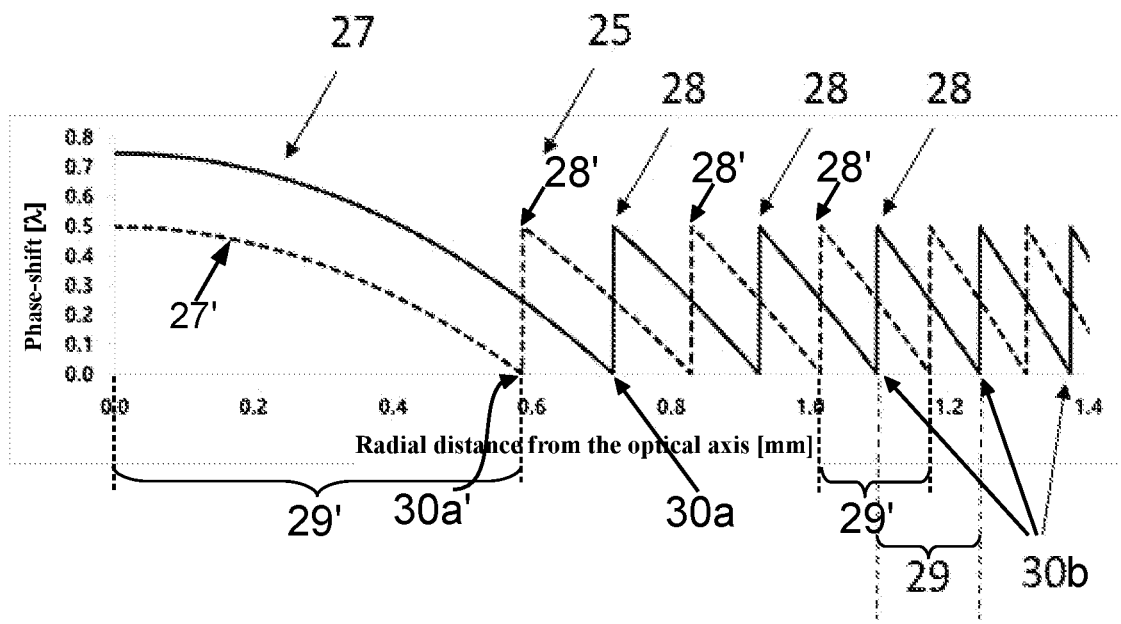
FIG. 3 also depicts the phase shift produced by a saw-tooth-type, non-apodized diffractive profile as a function of distance measured from the optical axis, where the maximum phase shift of the central zone is $3/4\lambda$.

FIG. 3 illustrates the phase shift of a saw-tooth-type, non-apodized diffractive profile 25 as a function of the distance measured from the optical axis 23, where the maximum phase shift of the central zone 27 is $3/4\lambda$, where phase shift means the phase shift in relation to the base defined by the base points 30a of the diffractive profile. The dashed line in the figure shows the original (conventional bifocal) profile, while the solid line illustrates the modification according to the invention.

The remaining figures show the change of optical performance (modulation transfer function, MTF) belonging to the embodiments according to FIGS. 2 and 3 as compared to the optical performance of a conventional bifocal profile. The MTF curve belonging to the diffractive profile 25 according to the invention is shown with a solid line, and the MTF curve belonging to a conventional bifocal profile with a dashed line. The MTF curves illustrate how the imaging quality changes as the object distance changes. The MTF curves obtained at various apertures are determined by the depth of focus depending on the aperture diameter and on the intensity distribution together.

Figure 4:
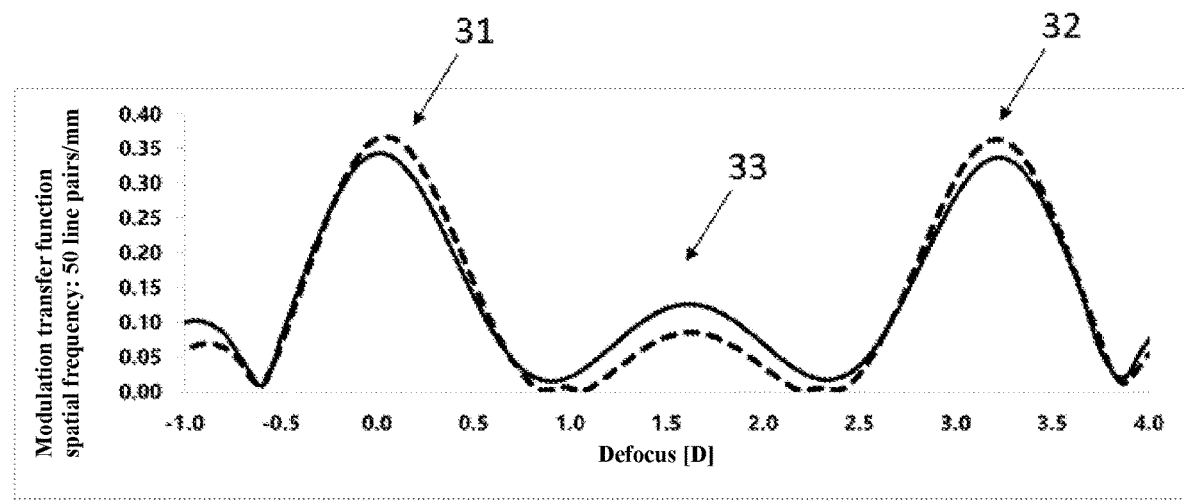
FIGS. 4 to 9 present the modulation transfer function (MTF) of the artificial ophthalmic lens containing the diffractive profile presented in FIGS. 2 and 3 as a function of distance measured from the focal point, at a spatial frequency of 50 lines/mm, but in the case of apertures of differing diameter, i.e. pupil size.

FIG. 4 shows the change of the optical performance of the artificial ophthalmic lens containing the diffractive profile 25 presented in FIG. 2, which is described by the modulation transfer function (MTF) as a function of distance measured from the point of focus, in the case of an aperture of 3.0 mm, and spatial frequency of 50 lines/mm.

Figure 5:
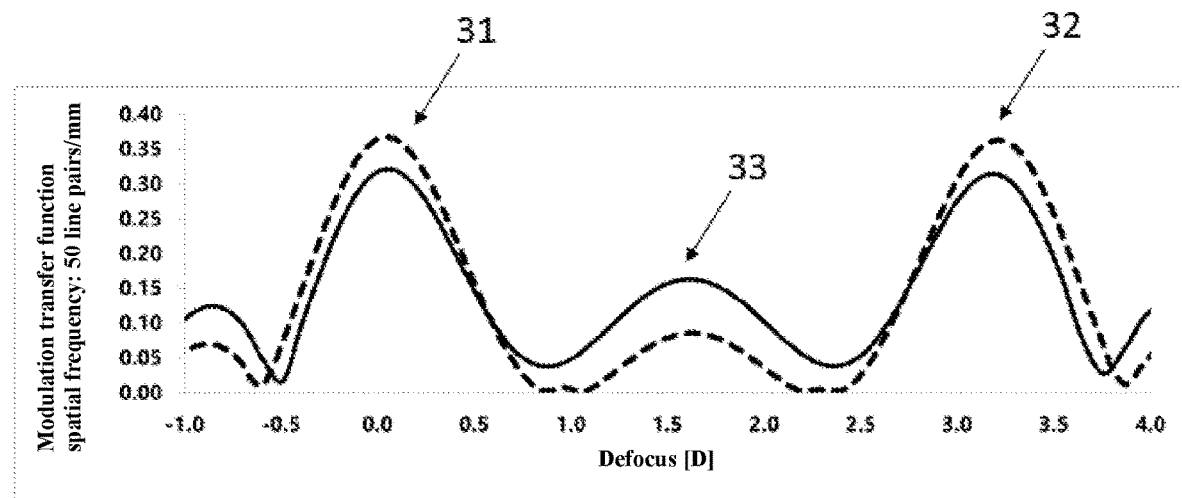

FIG. 5 shows the change of the optical performance (MTF) of the artificial ophthalmic lens containing the diffractive profile 25 presented in FIG. 3 as a function of distance measured from the point of focus, in the case of an aperture of 3.0 mm, and spatial frequency of 50 lines/mm.

Figure 6:
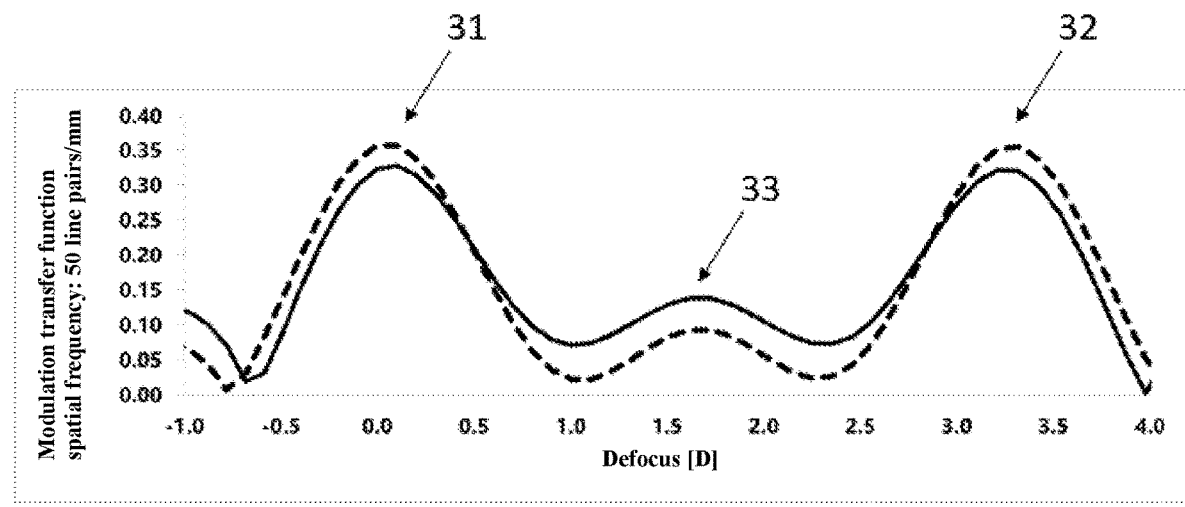

FIG. 6 shows the change of the optical performance (MTF) of the artificial ophthalmic lens containing the diffractive profile 25 presented in FIG. 2 as a function of distance measured from the point of focus, in the case of an aperture of 2.5 mm, and spatial frequency of 50 lines/mm.

Figure 7:
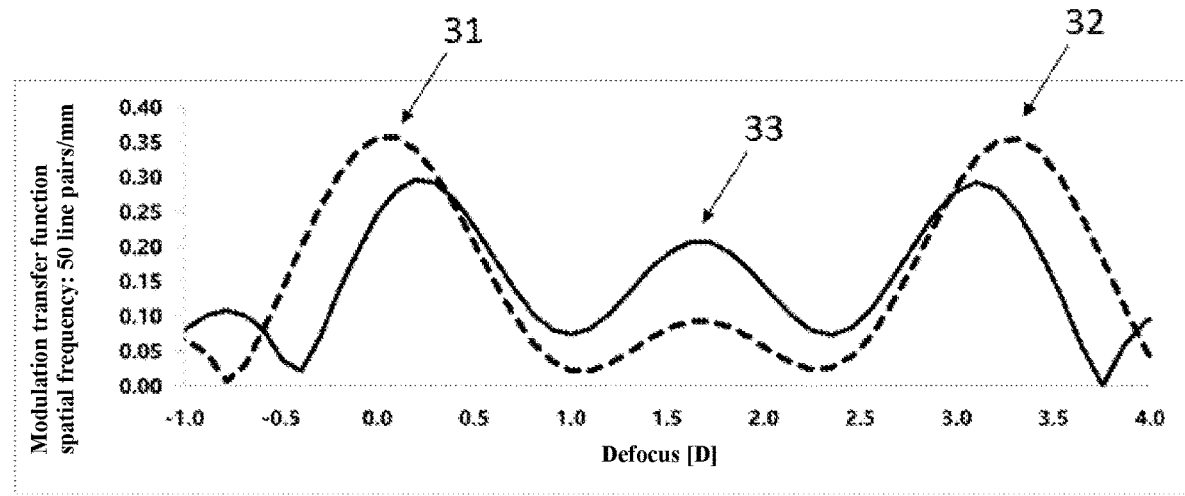

FIG. 7 shows the change of the optical performance (MTF) of the artificial ophthalmic lens containing the diffractive profile 25 presented in FIG. 3 as a function of distance measured from the point of focus, in the case of an aperture of 2.5 mm, and spatial frequency of 50 lines/mm.

Figure 8:
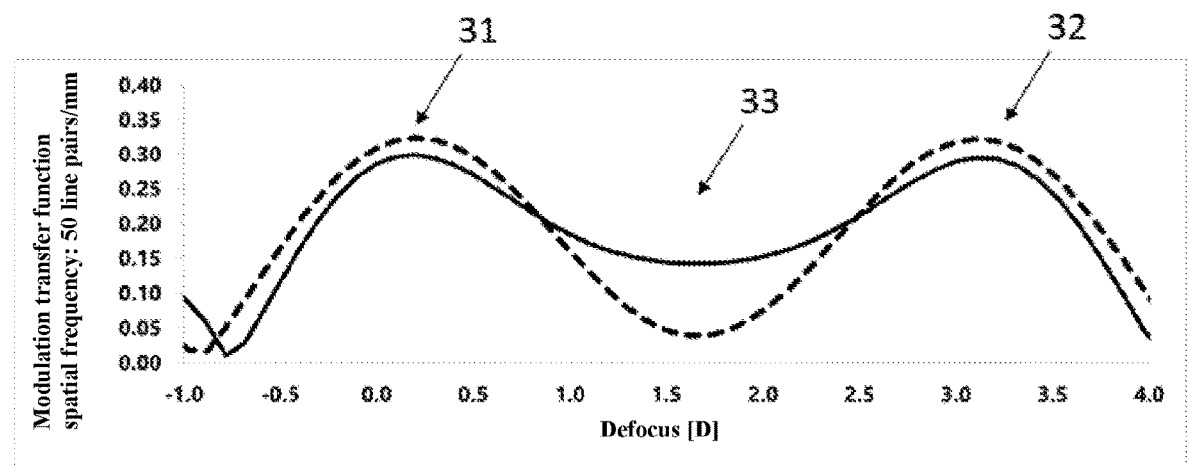

FIG. 8 shows the change of the optical performance (MTF) of the artificial ophthalmic lens containing the diffractive profile 25 presented in FIG. 2 as a function of distance measured from the point of focus, in the case of an aperture of 2.0 mm, and spatial frequency of 50 lines/mm.

Figure 9:
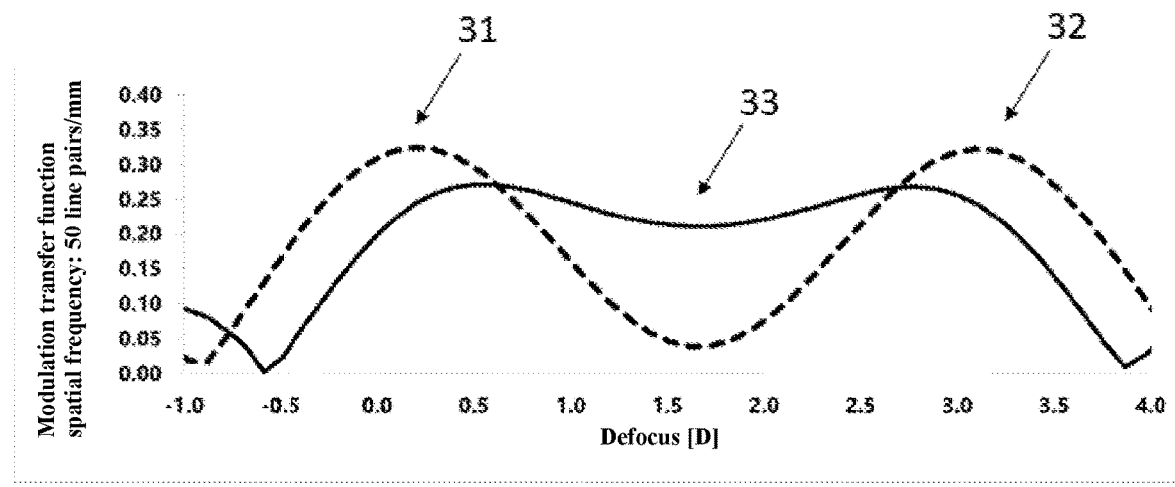

FIG. 9 shows the change of the optical performance (MTF) of the artificial ophthalmic lens containing the diffractive profile 25 presented in FIG. 3 as a function of distance measured from the point of focus, in the case of an aperture of 2.0 mm, and spatial frequency of 50 lines/mm.

In the aforementioned FIGS. 4 to 9 it can be seen that the optical performance curves also have a local side maximum between the two main maxima, which can be enhanced to produce an intermediate (intermediate distance) vision focal point 33 as well, thereby making it possible to produce a trifocal optical element.

A possible way of enhancing the intermediate vision focal point 33 falling between the focal points 31, 32 belonging to the $0^{th}$ and $1^{st}$ diffraction orders of the artificial ophthalmic lens containing the diffractive profile is the enhancement of the side maxima of the $0^{th}$ and $1^{st}$ diffraction orders and simultaneously ensuring their constructive interference. The essence of the present invention is the production of a diffractive profile 25 that enhances the side maximum of the focal point 31 belonging to the $0^{th}$ diffraction order and the side maximum the focal point 32 belonging to the $1^{st}$ diffraction order and by simultaneously ensuring their constructive interference by increasing the maximum phase shift of the central zone 27 to above $\lambda/2$.

A possible method of increasing the phase shift of the central zone 27 of the diffractive profile 25 to above $\lambda/2$ is increasing the central zone 27 of the diffractive profile 25 in such a way that the arc connecting the boundaries of the central zone 27 remains unchanged and the phase shifting zones 28 outside of the central zone 27 are shifted, while the areas 29 between the zone boundaries of the phase shifting zones 28 (i.e. the areas of the rings determined by the base points 30b of the individual phase shifting zones 28) outside of the central zone 27 remain unchanged, in other words the additional dioptric power characteristic of the phase shifting zones 28 remains unchanged. In other words the area of the central zone 27 is increased as compared to the areas 29 of the phase shifting zones 28 outside of it, which remain unchanged and remain the same as in the case of conventional bifocal profiles. In other words the central zone 27 occupies a larger area than the individual phase shifting zones 28, however, the arc of the central zone 27 is the same as the arc of a theoretical central zone 27' providing a phase shift of $\lambda/2$ and delimiting an area 29' that is the same size as the area 29 of the individual phase shifting zones 28. The arcs of the central zone 27 and of the theoretical central zone 27' are understood to mean arcs that run along the surface of the central zone 27 and along the surface of the theoretical central zone 27', respectively, and intersect the optical axis linking two base points 30a and 30a', respectively, (located on the opposite sides of the central zone 27 and the theoretical central zone 27', respectively) that fall on a straight line passing through the optical axis via the shortest path.

The designing of the diffractive profile 25 according to the invention may also take place accordingly. The starting point is a theoretical conventional bifocal diffractive profile that has a theoretical central zone 27' and theoretical phase shifting zones 28' outside thereof, and the size of the areas 29' between the zone boundaries of the theoretical phase shifting zones 28' is the same as the size of the area 29' delimited by the theoretical central zone 27'. In the case of the theoretical diffractive profile the phase shift of at least the theoretical central zone 27' is $\lambda/2$, but in the present case the phase shift of every phase shifting zone 28' of the initial theoretical diffractive profile is $\lambda/2$. The two useful focuses of the theoretical bifocal diffractive profile are selected so that the two useful focuses belonging to the $0^{th}$ and the $1^{st}$ diffraction order substantially coincide with the focal points 31, 32 belonging to the $0^{th}$ and $1^{st}$ diffraction orders of the diffractive profile 25 of the artificial ophthalmic lens to be produced (which focal points 31, 32 in the present case are a distant focus set to infinity and a near focus set to approx. 30 cm). Such a conventional bifocal diffractive profile can be designed easily based on design values taken from the prior art literature. As compared to the theoretical bifocal diffractive profile the phase shift of the central zone 27 is increased to above $\lambda/2$, while maintaining the arc linking the base points 30a of the central zone 27 unchanged, in other words the central zone 27 is increased in the direction perpendicular to the optical axis so that in the meantime the arc (passing through the optical axis) delimiting the central zone 27 and linking its base points 30a remains parallel to the arc linking the base points 30a' (and passing through the optical axis) of the theoretical central zone 27'. In the meantime the phase shifting zones 28 outside of the central zone 27 are shifted in a direction perpendicular to the optical axis 23 in such a way that the areas 29 between the zone boundaries of the phase shifting zones 28 remain unchanged.

Comparing FIGS. 5, 7 and 9 with FIGS. 4, 6 and 8 it can be determined that the greater phase shift increase resulted in a more significant intermediate focus in the case of 3.0 and 2.5 mm apertures, and led to a significant extended depth of focus in the case of small pupil diameters, which effect did not appear at all in the case of conventional bifocal lenses. It was found that the intermediate distance focus and the extended depth of focus appearing in the case of small pupil diameters is especially significant in case the maximum phase shift of the central zone 27 is about $3/4\lambda$, but an improvement over the conventional bifocal profile can be observed everywhere in case the maximum phase shift of the central zone 27 is greater than $\lambda/2$ and smaller than $\lambda$.

Already at a maximum phase shift of a value of 0.52λ the effect is of such an extent that it provides an improvement in the optical performance of the lens perceived by the users. Preferably the maximum phase shift of the central zone 27 in the diffractive profile 25 falls within the range of 0.52λ-0.8λ, especially preferably in the range of 5/8λ and 3/4λ.

The performance of the present invention is not limited by the characteristics of the diffractive profile 25 outside of the central zone 27. The diffractive profile 25 outside of the central zone 27 may be apodized or non-apodized, an external, purely refractive area can also be attached to the diffractive profile 25. If the diffractive profile 25 outside of the central zone 27 is to be apodized, then in the design stage it is preferred to start from a theoretical bifocal diffractive profile wherein the maximum phase shift of the central zone 27' continues to be λ/2, but the theoretical phase shifting zones 28' outside of the central zone 27' are apodized, in other words their maximum phase shift is varying (increasing or decreasing).

On the basis of the present invention a diffractive profile may also be realised that creates a lens with trifocal optical performance by enhancing a side maximum occurring between any two consecutive diffractive orders (such as the +1$^{st}$ and +2nd orders).

A further advantage of the present invention is that in addition to trifocal optical performance, the artificial ophthalmic lens comprising the diffractive profile 25 presented in the figures also ensures extended depth of focus optical performance in the case of small pupil diameters occurring in photopic conditions (through-focus curves measured in the case of a 2.0 mm aperture), as can be observed in FIGS. 8 and 9.

The invention claimed is:

1. A trifocal artificial intraocular lens (IOL) (20), which contains an anterior side optical surface (21), a posterior side optical surface (22) and an optical axis (23), at least one of the anterior side optical surface (21) and the posterior side optical surface (22) contains a diffractive profile (25) having three useful focal points, wherein the three useful focal points correspond to focal points (31, 32) belonging to the 0th and 1st diffraction orders of the diffractive profile, and to a focal point (33) belonging to an enhanced diffractive secondary peaks between the focal points (31, 32) belonging to the 0th and the 1st diffraction orders, wherein the secondary peaks are enhanced such that a maximum phase shift of a central zone (27) of the diffractive profile (25) is greater than λ/2, where the phase shift means the phase shift relative to a base defined by base points (30*a*) of the central zone of the diffractive profile (25), wherein areas (29) between zone boundaries of individual phase shifting zones (28) are identical in size, and a first arc linking the base points (30*a*) of the central zone (27) on the diffractive profile (25) is selected so that it is parallel with a second arc corresponding to a theoretical central zone (27') having a maximum phase shift of λ/2 and having an area (29') which is the same as the areas (29) occupied by the individual phase shifting zones (28).

2. The artificial intraocular lens according claim 1, characterised by that the maximum phase shift of the central zone (27) is greater than λ/2 and smaller than λ.

3. The artificial intraocular lens according to claim 1, characterised by that the maximum phase shift of the central zone (27) is greater than λ/2 and smaller than or equal to 3/4λ.

4. The artificial intraocular lens according to claim 1, characterised by that the diffractive profile outside of the central zone (27) is apodized.

5. The artificial intraocular lens according to claim 1, characterised by that a peripheral, purely refractive portion is peripherally connected to the diffractive profile (25).

6. The artificial intraocular lens according to claim 1, wherein the maximum phase shift of the central zone (27) is 5/8λ.

* * * * *